United States Patent [19]

Trager et al.

[11] 4,421,748

[45] Dec. 20, 1983

[54] ARTIFICIAL TEAR AID

[76] Inventors: Seymour F. Trager, 14 Sherwood Dr., Plainview, N.Y. 11803; Victoria S. Chylinski, 11 Peghouse Rise, Slad Road, Stroud, Glos., England

[21] Appl. No.: 397,914

[22] Filed: Jul. 13, 1982

[51] Int. Cl.³ .................... A61K 31/685; A61K 31/74
[52] U.S. Cl. ...................................... 424/199; 424/78
[58] Field of Search ................................ 424/199, 78

[56] References Cited

U.S. PATENT DOCUMENTS

| | | | |
|---|---|---|---|
| 2,064,727 | 12/1936 | Buer | 424/199 |
| 3,062,721 | 11/1962 | Grate | 424/199 |
| 3,608,073 | 9/1971 | Phares et al. | 424/168 |
| 4,250,173 | 2/1981 | Cantello | 424/248.51 |
| 4,252,793 | 2/1981 | Altman | 424/199 |

OTHER PUBLICATIONS

Int. Ophthal. Clin. 13, 145–153 (1973)–Lemp. "Tear Substitutes in the Treatment of Dry Eyes" The Merck Index–9th ed. item 5287–1976 Merck & Co.

*Primary Examiner*—Douglas W. Robinson
*Attorney, Agent, or Firm*—Fidelman, Wolffe & Waldron

[57] ABSTRACT

An artificial tear composition comprising a sterile, aqueous hypotonic solution of lecithin and a viscosity-adjusting agent.

7 Claims, No Drawings

ARTIFICIAL TEAR AID

This invention relates to artificial tear formulations. More particularly, this invention relates to artificial tear formulations particularly suitable for the alleviation of dry eye conditions.

A diminution of the quantity of tears produced and distributed through the lachrymal ducts or a decrease in the stability of the tear film produced, results in a condition of the eye referred to as dry eye. Dry eye states act to decrease visual acuity, produce discomfort ranging from mild to intense and eventually, if allowed to remain untreated and uncorrected, result in permanent damage with degradation of the exposed ocular tissues, with a complete breakdown of corneal tissue necessitating, in the extreme, corneal transplants.

There have been no diagnostic method findings associated with these dry eye states. Rather, therapy is usually predicated on the symptoms rather than on results of objective testings. Thus, in the consideration of dry eye states, replenishment or buttressing of the deficient tear flow or certain tear components is necessary to prevent permanent damage to the ocular tissue.

BACKGROUND OF THE PRIOR ART

The condition of dry eye is not new and various compositions for treating dry eye have been proposed and put into use over the years. For example, the treatments employed by ancient Greek physicians for this condition dominated medical practice throughout the Middle Ages and into the nineteenth century. The selection of components for ancient collyria, or for any of the eye treatment preparations of the time, suggests either an instinctive or empirical knowledge of the composition of tears and tear films. Egg whites, very rich in albumen which is a major tear protein, and goose fat, a lipid admixture which, like meibomian lipids, become fluid at temperatures approximating normal body temperatures.

Use has also been made of substances which serve to induce a measure of irritation, presumably to induce reflex tearing. Such substances as alcohols, acetic acid values of vinegar, onion fermentates and the like have been utilized in this approach. Obviously, such methods are less than totally acceptable.

Other solutions offered for the alleviation of dry eye in more recent years, i.e., during the 19th century and early 20th century, have included aqueous solutions of common table salt, glycerol, various oils, and isotonic solutions of various salts, known as Ringer's and Locke's solutions.

Approximately thirty years ago, the employment of aqueous solutions of inert, substituted cellulose ethers such as methyl cellulose was proposed, and such formulations are currently in use. Other substituted cellulose ethers such as hydroxyethyl cellulose, hydroxypropyl methyl cellulose, and hydroxypropyl cellulose have been subsequently utilized as polymeric components in artificial tear formulations. Each of these polymerics imparts high viscosities to the tear formulations, even when employed in relatively low concentrations as, for example, on the order of from about 4 to about 500 CPS. It has been this impartation of high viscosity to the formulations which has been believed to prolong retention time of the tear substitute in the fornices and over the preocular surface.

However, it has been subsequently demonstrated that the ocular retention time is not a direct function of the vehicle viscosity. Further, the use of highly viscous polymeric solutions also results in unpleasant side effects to the user thereof. For example, insufficient lubrication of the lids and the tendency for encrustations to form at the lid margins produces irritation and discomfort.

Subsequently, other hydrophilic polymerics such as polyvinyl alcohol and polyvinyl pyrrolidone, among others, combining good film-generating properties with relatively low viscosities in aqueous solution. Such formulations, however, remain less than satisfactory inasmuch as they do not provide good wettability.

It is an object of the present invention to provide an artificial tear formulation.

Another object of the present invention is to provide an artificial tear formulation which in use will effectively alleviate dry eye symptoms.

A further object of the present invention is to provide an artificial tear formulation which is non-contaminating and non-interferring with visual clarity.

STATEMENT OF THE INVENTION

According to the present invention, there is provided an artificial tear composition comprising a sterile, hypotonic aqueous solution of lecithin and a viscosity-adjusting agent.

Suitable formulations contain lecithin, preferably lecithin sulfate, in an amount of from about 1.0 to about 20 percent weight/volume, preferably in an amount of from 5.0 to about 10 percent weight/volume.

The viscosity-adjusting agent of the composition is present in amounts of from about 0.1 to about 20 percent weight/volume, preferably in amounts of from about 2.5 to about 5.0 percent weight/volume. It has been found that suitable viscosity-adjusting agent for the purposes of this invention are those selected from methyl cellulose, hydroxypropyl cellulose polyvinyl alcohol and hydroxyethyl cellulose. The preferred viscosity-adjusting agent is hydroxyethyl cellulose.

It has been found that such compositions not only possess surface tensions approximating those of natural tears, providing corneal wetting, but additionally spread uniformly over the coated surface.

The tonicity of the artificial tear composition may be adjusted to the desired values by the addition thereto of sodium chloride or other soluble salts, such as potassium chloride, in amounts sufficient to impart the desired tonicity thereto. Other tonicity adjusting agents, such as dextrose, and sorbitol may also be advantageously employed, in combination with water-soluble salts. Suitable tonicity values are achieved by the inclusion of the tonicity-adjusting agent, or agents, in amounts of from about 1 to about 5 percent weight/volume.

Preferably, the basic compositions include such additional components as non-ionic surfactants and sequestering, preservative and buffering agents.

Suitably, a non-ionic surfactant such as polyoxyalkylene oleic esters of sorbitol anhydrides may be included in amounts of from about 2 to about 10 percent weight/volume.

Disodium edatate, citric acid, sodium citrate and the like, or combination thereof, in amounts of from about 0.5 to about 2 percent weight/volume, are suitable as sequestering agents in the present compositions. Disodium edatate is particularly desirable, providing as it does a measure of protection against pseudomonal contamination while additionally functioning as a chelating or water-softening agent.

Suitable preservative agents include sodium ethylmecurithiosalicylate, benzalkonium chloride or the like, present in amounts of from about 0.004 to about 0.02 percent weight/volume.

As buffering agents, alkali metal phosphates such as sodium and potassium phosphate, or mixtures thereof, are particularly suitable for use in the present compositions, generally present in amounts of from about 0.1 to about 1.0 percent weight/volume.

Formulation of the artificial tear compositions may be effected in any convenient manner known to the art, such as by simply admixing the desired amount of the specified ingredients and providing the necessary amount of sterile water to provide the necessary dilution.

The compositions of the present invention, instilled drop-wise in the eye, swells the tear meniscus, and, with normal blinking, the tear meniscus becomes thoroughly admixed with the tear film, the flooded tear meniscus returns to its steady-state size and the superficial lipid layer is reestablished over the aqueous layer. Moreover, the artificial tear composition interacts favorably with both the superficial lipid layer and the underlying mucous layer, enhancing film stability.

The compositions of the present invention have been found to lower the surface tension of the tear film by increasing the film pressure of the lipid without interfering with the integrity thereof, the film pressure of an insoluble film such as lipid over water being defined as the difference between the surface tension of the pure water surface and that of the lipid-covered water surface.

Further, the compositions of the present invention do not mix with tear biopolymers, by aggregate formation or by denaturation, and do not adversely affect the clarity of the aqueous tear layer.

Finally, the compositions do not contribute to hydrophobic contamination of the mucus layer, but on the contrary, are capable of forming a hydrophilic layer in the absence of a functional mucus layer, having all of the functional properties of a normal mucus layer.

The compositions of the present invention, topically applied, provides relief for both aqueous-deficient and mucus-deficient eyes; provide highly effective lipid-masking and scavenging layers, effective also therapeutically in situations where lipid abnormalities exist.

Use of the artificial tear compositions is conveniently effected by instilling the composition, drop-wise, into the eye or eyes of the user.

A specific example of the composition of this invention is set forth below:

EXAMPLE 1

| Ingredient | Amount |
| --- | --- |
| Lecithin | 2.0 mg |
| Hydroxyethylcellulose | 43.0 mg |
| Tween 80 | 7.5 mg |
| Disodium edatate | 15.75 mg |
| Sodium Chloride | 34.2 mg |
| Sodium Phosphate, dibasic | 87.5 mg |
| Thimerosal | 0.428 mg |
| Potassium phosphate, mono | 25.0 mg |

-continued

| Ingredient | Amount |
| --- | --- |
| Distilled water | to 10.0 ml |

The artificial tear solution was subjected to ocular irritation studies. Drops were instilled into the right eyes of six normal adult albino rabbits, with the drops being instilled three times daily over a period of 21 days. The appearance of the eyes was noted before, immediately after and one minute after the instillation of the drops. At weekly intervals, a complete slitlamp evaluation was conducted, including corneal clarity, anterior chamber reaction, iris appearance and the presence or absence of conjunctival infection. The upper and lower lids of the rabbits were everted and the presence or absence of follicles and/or papillae noted.

The left eye of each rabbit served as a normal control. Five eyes exhibited minimal transient injection after two weeks which did not appear to be drug-related. No papillae or discharge was noted at any time and at all times the cornea, anterior chamber, iris and lens of each rabbit remained totally normal. Each rabbit remained healthy throughout the study and exhibited no gross change in weight.

Following the testing period, gross examination of the eyes was completely within normal limits.

The invention, in its broader aspects, is not limited to the specific details shown and described, and departures may be made from such details without departing from the principles thereof and without sacrificing the chief advantages thereof.

What is claimed is:

1. An artificial tear composition comprising a sterile hypotonic aqueous solution containing from about 1.0 to 20 percent weight/volume lecithin and from about 0.1 to about 20 percent by weight of a viscosity-adjusting agent selected from the group consisting of methyl cellulose, hydroxypropyl cellulose, polyvinyl alcohol and hydroxyethyl cellulose.

2. A composition as defined by claim 1 wherein said viscosity-adjusting agent is hydroxyethyl cellulose.

3. A composition as defined by claim 1 wherein said lecithin is lecithin sulfate.

4. A composition as defined by claim 2 wherein said hydroxyethyl cellulose is present in an amount of from about 0.1 to about 2 percent weight/volume of the composition.

5. A composition as defined by claim 1 further including a sequestering agent, a preservative agent, a buffering agent and a non-ionic surfactant.

6. A composition as defined by claim 5, wherein said sequestering agent is disodium edatate, said preservative agent is sodium ethylmercurithiosalicylate, said non-ionic surfactant is a polyoxyalkylene oleic ester of sorbitol anhydride and said buffering agent is selected from sodium and potassium phosphate and mixtures thereof.

7. A composition as defined by claim 5 wherein said non-ionic surfactant is present in an amount of from about 2 to about 10 percent weight/volume, said sequestering agent is present in an amount of from about 0.5 to about 2 percent weight/volume, said preservative agent is present in an amount of from about 0.004 to about 0.02 percent weight/volume and said buffering agent is present in an amount of from about 0.1 to about 1.0 percent weight/volume.

* * * * *